US008768600B2

(12) United States Patent
Blanc et al.

(10) Patent No.: US 8,768,600 B2
(45) Date of Patent: Jul. 1, 2014

(54) AUTOMOTIVE-VEHICLE-BORNE MINIATURE SPECTROMETER HAVING A SINGLE MEASUREMENT AND REFERENCE DETECTOR

(75) Inventors: Jeremie Blanc, Aussaune (FR); Benjamin L'Henoret, Paris (FR); Laureen Merlina-Bonnafous, Toulouse (FR)

(73) Assignee: Continental Automotive France, Toulouse (FR)

( * ) Notice: Subject to any disclaimer, the term of this patent is extended or adjusted under 35 U.S.C. 154(b) by 454 days.

(21) Appl. No.: 13/141,505

(22) PCT Filed: Dec. 15, 2009

(86) PCT No.: PCT/EP2009/008999
§ 371 (c)(1),
(2), (4) Date: Sep. 7, 2011

(87) PCT Pub. No.: WO2010/072363
PCT Pub. Date: Jul. 1, 2010

(65) Prior Publication Data
US 2011/0313635 A1    Dec. 22, 2011

(30) Foreign Application Priority Data
Dec. 23, 2008  (FR) ..................... 08 07379

(51) Int. Cl.
*G01J 3/44* (2006.01)
*G01J 1/42* (2006.01)
*G01J 3/42* (2006.01)

(52) U.S. Cl.
CPC ................. *G01J 1/4257* (2013.01); *G01J 3/42* (2013.01); *G01F 3/0232* (2013.01)
USPC ......................................... 701/102; 356/319

(58) Field of Classification Search
CPC .......... G01J 1/4257; G01J 3/42; G01J 3/0232
USPC .................. 701/102, 101, 114; 356/319, 326, 356/432–440; 702/116; 73/114.38
See application file for complete search history.

(56) References Cited

U.S. PATENT DOCUMENTS 3,335,285 A * 8/1967 Gally, Jr. et al. ............... 250/221
3,667,851 A * 6/1972 Alm ................................ 56/427

(Continued)

FOREIGN PATENT DOCUMENTS

| WO | 90/02936 A1 | 3/1990 |
| WO | 91/11702 A1 | 8/1991 |
| WO | 03/030621 A2 | 4/2003 |

OTHER PUBLICATIONS

Jouko M. et al. "LED-based NIR spectrometer module for hand-held and process analyser applications", Sensors and Actuators B 51 (1998) 220-226, Received Mar. 30, 1998, received in revised form Jun. 9, 1998, accepted Jun. 16, 1998.

(Continued)

*Primary Examiner* — Mahmoud Gimie
(74) *Attorney, Agent, or Firm* — Young & Thompson (57) ABSTRACT

A device for measuring a spectrum of a light beam, in a wavelength range chosen beforehand, the spectrum being generated by a sample to be analyzed, the optical measuring device including at least one light source, a measurement cell and a measurement detector placed on a measurement optical pathway, the measurement optical pathway being taken by a measurement optical beam emitted by the light source, and encountering the measurement cell, a self-calibration unit allowing any drift of the light sources, due to environmental conditions or conditions of use, to be taken into account independently of whether a sample to be analyzed is present in or absent from the measurement cell, the self-calibration unit including elements for creating a reference optical pathway, taken by a reference optical beam emitted by the light source, and not encountering the measurement cell, and a reference detector.

20 Claims, 5 Drawing Sheets

(56) References Cited

U.S. PATENT DOCUMENTS

| | | | |
|---|---|---|---|
| 4,444,499 A * | 4/1984 | Akiyama et al. | 356/325 |
| 4,594,968 A | 6/1986 | Degobert et al. | |
| 4,640,621 A | 2/1987 | Rose | |
| 5,113,073 A * | 5/1992 | Szepan | 250/343 |
| 5,241,367 A | 8/1993 | Grob et al. | |
| 5,348,002 A * | 9/1994 | Caro | 600/310 |
| 5,739,916 A * | 4/1998 | Englehaupt | 356/414 |
| 5,754,289 A * | 5/1998 | Ozaki et al. | 356/301 |
| 6,081,481 A * | 6/2000 | Sabatier et al. | 367/8 |
| 6,246,481 B1 * | 6/2001 | Hill | 356/487 |
| 7,593,107 B2 * | 9/2009 | Wolf et al. | 356/432 |
| 2003/0025909 A1 * | 2/2003 | Hallstadius | 356/436 |
| 2008/0151248 A1 * | 6/2008 | Cole et al. | 356/437 |

OTHER PUBLICATIONS

Norbert Neumann et al.: "Tunable infrared detector with integrated micromachined Fabry-Perot filter", MOEMS and Miniaturized Systems VI, Jan. 2007, Chemnitz Univ. of Technology, Center for Microtechnologies, Chemnitz, Germany Fraunhofer Institute for Reliability and Microintegration, Chemnitz, Germany.

International Search Report, dated Feb. 22, 2010, from corresponding PCT application.

* cited by examiner

AUTOMOTIVE-VEHICLE-BORNE MINIATURE SPECTROMETER HAVING A SINGLE MEASUREMENT AND REFERENCE DETECTOR

BACKGROUND OF THE INVENTION

1. Field of the Invention

The present invention relates to the field of automotive-vehicle-borne electronics. More particularly it relates to optoelectronic instruments. More specifically, it relates to spectrometry suitable for determining the composition of a fluid.

2. Description of the Related Art

Competition between the various automobile manufacturers leads to an unceasingly renewed pursuit of better operational performance, in terms of both fuel economy and ecological characteristics. In the field of vehicles powered by internal combustion engines, the composition of the fuel has a direct impact on the performance of the engine. Consequently, knowing the precise composition of the fuel allows certain of the operating parameters of the engine to be adjusted to improve combustion and render the vehicle less polluting.

Moreover, this knowledge may also allow detection of mistakes (filling a petrol tank with diesel and vice versa) that could possibly damage the engine, and may allow a warning to be sent to the driver or the ignition to be blocked so as to prevent irreparable damage. Analogously, it allows detection of a fuel that does not meet legal quality standards.

Analogous observations apply to the engine oil, even to the coolant or to other fluids the properties of which influence the operation of the vehicle.

One means of achieving this compositional analysis of a fluid is to use spectrometric technology.

It is recalled that a spectrometer is a measurement instrument intended to determine the absorption of certain wavelengths of the spectrum (generally of light) by a sample to be analyzed. The wavelengths absorbed form peaks in the absorption spectrum and characterize certain molecules or components present in the sample.

As defined in the context of the present invention, an optical spectrometer is therefore mainly composed of a light source, an optical assembly for forming the light beam so as to create a parallel beam able to pass through the sample, a wavelength filter allowing measurement in a certain wavelength range, and a light detector which measures the light intensity received at this wavelength.

Spectrometers working in the ultraviolet, visible and near infrared wavelength ranges are already in day-to-day use in many fields. Among these fields mention may be made of:
  agriculture and food production (for example for monitoring the moisture content of cereal grains, the maturity of fruits, the fat contained in certain foods, etc.);
  biomedicine (for example for measuring blood sugar level without taking a sample, etc.); and
  fuel production (controlling the quality and the composition of the crude oil, controlling the quality of the end products such as gasoline, diesel, etc.).

All these fields of application use the same type of measurement instrument, only the size and portability characteristics of which vary. Such instruments optionally use various technologies (Fourier transform, filter, monochromator, diffraction system, etc.) and do not operate over a wide temperature range.

This is because, for reasons related to drift in their performance depending on the temperature, they are rarely used in environments that experience large temperature variations. These are moreover often laboratory-based instruments, or in any case require easy access to their components for maintenance of the detector or of the light source (the lifetime of which is often short, or in any case shorter than the fifteen or so years necessary in the automobile-borne environment). Consequently, they are unsuitable for long-term installation in an environment that is practically inaccessible for maintenance.

Finally, these spectrometers are not subject to demanding unit production costs, and therefore top-of-the-range components are often used, for example tungsten-halogen or filament lamps that are very temperature-stable but which are incompatible with installation in mass-produced automotive vehicles.

It is understood that these questions, of temperature drift, of component reliability and therefore of access for maintenance, and finally of manufacturing cost, make these commercially available spectrometers unsuitable for use in automobiles and comparable environments.

In an application such as that considered in the field of monitoring automobile fluids, it is necessary to use very low unit cost components that are robust over time, so as to guarantee a lasting operation. One solution is to use light emitting diodes (LEDs) as the light source.

In fact, light emitting diodes are very reliable, well-known components that have a very low cost because they are used in very high volumes in a multitude of applications. They are moreover at the present time available in many wavelength versions, allowing their use in a spectral range from 300 nm (near ultraviolet) to 2500 nm (near infrared).

Figure 1:
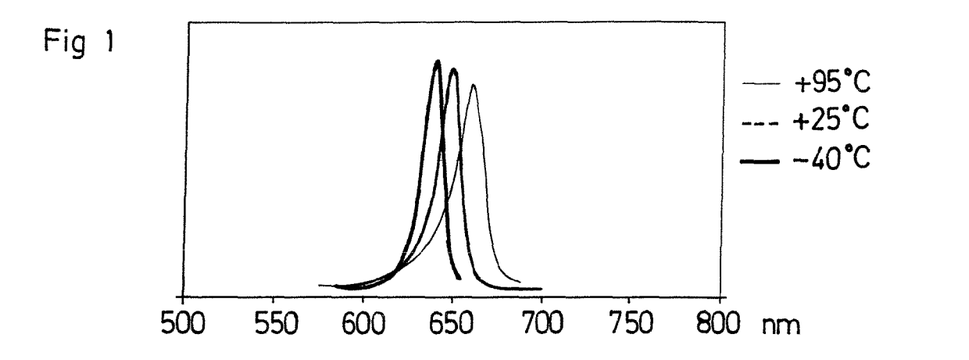
FIG. 1 illustrates the spectral properties of a light emitting diode (LED) as a function of temperature, demonstrating the shift of the emission spectrum in wavelength and in emitted power.
Figure 2:
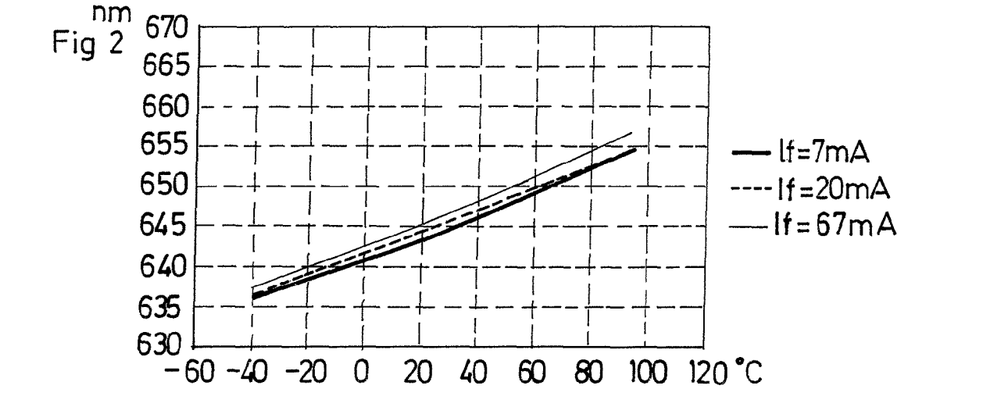
FIG. 2 likewise illustrates the peak wavelength shift of a light emitting diode as a function of temperature and of the current flowing through the light emitting diode.
Figure 3:
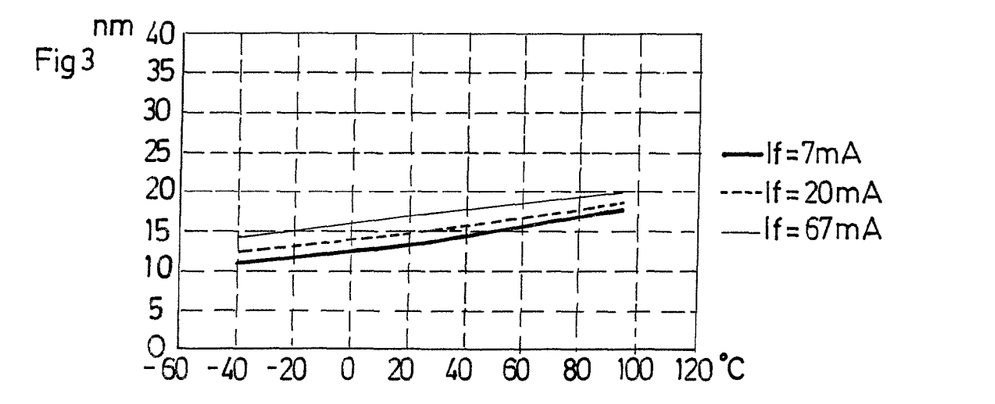
FIG. 3 likewise illustrates the peak width at half-maximum of the spectrum of the light emitting diode as a function of temperature and of the current flowing through the light emitting diode.
Figure 4:
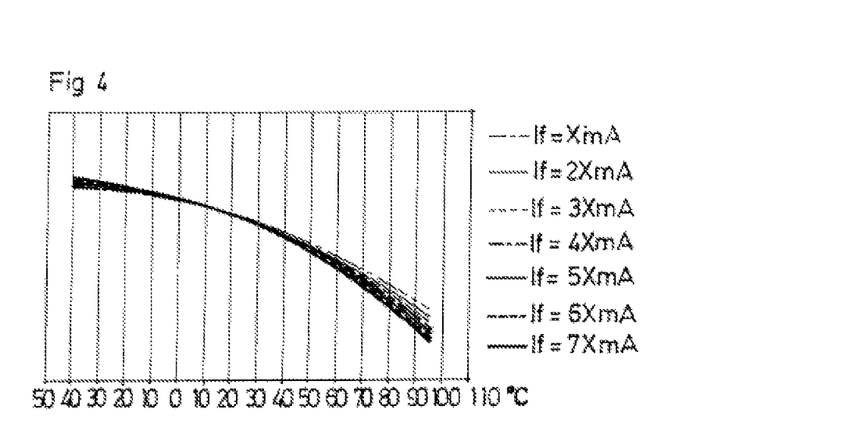
FIG. 4 shows the luminous power emitted for various values of current flowing through the light emitting diode between about −40° C. and +95° C.

As may be seen in FIG. 1, the light emitting diodes generally have a fairly wide spectrum characterized by a width at half-maximum from 35 nm to more than 100 nm. It is thus possible, by combining a number of diodes having different properties, to create a source having a very wide emission spectrum.

The emission spectrum and optical power properties of the light emitting diodes may vary substantially depending on the current flowing through them and the ambient temperature in which they are used (see FIGS. 1, 2, 3 and 4 for an example of the value measured for a light emitting diode at 650 nm). And yet, interpretation of the measured absorption requires the intensity, at a given wavelength, of the light wave sent through the sample analyzed to be known precisely.

Their use as a light source for spectroscopy, in environments the temperature of which may vary significantly (for example from −40° C. to +105° C. in an automobile), therefore requires innovative solutions in order to compensate for the natural variation in their properties. More generally, these observations relate to all light sources whose performance varies with aging and temperature.

Low-cost spectrometer devices using an LED-based technology are already known. Several devices of this type are currently patented and commercially available.

One of these devices is marketed by Zeltex and described in patent U.S. Pat. No. 6,369,388 B2. It is a portable spectrometer working in the near infrared intended mainly for analyzing the quality of harvested grain. Various applications are envisioned for the device described, ranging from the biomedical field to agriculture and food production and to fuels.

Among the applications proposed for this device, mention is made of measurement of the octane rating of a gasoline using a discrete spectrum obtained by measuring absorption at 14 different wavelengths, this constraint corresponding to a legal quality standard for fuels distributed by gas stations in an American state.

The Zeltex spectrometer uses the same absorption measurements in its various applications, and therefore independently of the sample analyzed.

The range of temperatures of operation delivering a measurement of guaranteed reliability ranges from −20° C. to +55° C. Such an operating range is incompatible with use in an automobile-borne environment for which the sensors must be rated for temperatures lying between −40° C. and +105° C.

Two methods are presented in the same patent U.S. Pat. No. 6,369,388 B2 for compensating for the effect of temperature.

A first method envisions compensating the results of the spectral absorption measurements depending on the temperature measured by a sensor using a preinstalled compensation algorithm. This method does not attempt to prevent temperature-related deformations of or drifts in the components but attempts to correct the measured values using a previously established correction curve.

A second method considered in the context of this Zeltex device uses a self-calibrating spectrometer. This is then a true compensation of the variations caused by temperature and by aging of the components of the series of measurement units, and in particular the light emitting diodes.

In this method, before each spectral measurement is acquired, the measurement cell is emptied, a first measurement is carried out with the light source turned off ("0" light measurement) which characterizes the measurement noise due to the electronics and the detector, which varies with environmental conditions and time. Then a second measurement is carried out with the light turned on, still without a sample in the cell, thus delivering a "100" light measurement, also affected by the environmental conditions of the measurement.

These two successive measurements allow the spectrometer to self calibrate. However, the constraint of having to empty the cell for this procedure is incompatible with a vehicle-borne use, for example, and, as will be readily appreciated, with permanent installation in a fuel tank or in a fuel distribution circuit.

Another device, designed and manufactured by Rikola, relates to a spectrometer intended for use in a laboratory. This spectrometer may also be employed in an environment the temperature of which varies between 5 and 55° C., too narrow with respect to the constraints of the automobile environment.

It measures the absorption at 32 determined wavelengths. To do this, it uses a monochromator wavelength filter, placed on the source side of the spectrometer, and formed by a diffraction system and 32 light emitting diodes (LEDs). These light emitting diodes are placed on chosen points allowing the desired wavelengths to be obtained.

With the aim of better compensating for the effect of temperature variations on the components of the spectrometer, and thus on the quality of the measurements delivered, the Rikola device allows "0" light and "100" light measurements to be carried out without the sample to be analyzed being present. A calibration of the apparatus is thus obtained.

However, a significant temperature variation results in a deformation of the hardware and therefore movement of the light emitting diodes, which modifies the wavelengths created by the diffraction system and light emitting diode assembly.

Consequently, the spectrometer uses a Peltier device to ensure a sufficiently precise measurement in the temperature range considered, from 5° to 55° C., by regulating the temperature of the grating and light emitting diodes about 30° C. This limits the conditions of use that may be envisioned for the spectrometer.

Moreover, and in contrast to the preceding device, the spectrometer is not associated with a processing algorithm for processing the measured spectrum.

A third low-cost spectrometer device has been developed by Sentelligence, and is for example described in document WO 2003 030 621 A2.

This spectrometer, intended to be vehicle-borne, is produced in the form of an integrated component comprising a light source in the form of light emitting diodes, a truncated conical shaped optic placed in contact with the sample to be analyzed, and a detector placed substantially in the plane of the light source.

It allows the absorption to be measured at various wavelengths. It is not a transmission spectrometer as the two other spectrometers mentioned were, but a reflection spectrometer. It therefore uses measurement of the spectrum reflected from said sample subjected to a known light source to characterize the components present in the sample, and not of its absorption spectrum. Such a choice of reflection spectrometer technology is envisioned for relatively opaque products, which absorb the light rays very strongly (soot, etc.).

The light source is formed by combining light emitting diodes each chosen depending on the wavelengths of which the reflection, by the sample to be analyzed, it is desired to measure. Filters are placed on the side of the light source, so as to limit the beam which passes through the sample to be analyzed to a certain optical wavelength band, and the emission intensity level is optionally controlled by a photodiode (reference detector), placed on an optical pathway independent of the sample to be analyzed.

"0" light (light turned off so as to measure electronic noise) and "100" light (light turned on) measurements may be carried out without the sample to be analyzed being removed from the measurement cell.

This is achieved by correcting the intensity measured at the photodiode so as to calculate an intensity that the measurement detector would theoretically receive if the sample were absent.

By allowing the measurement detector to be calibrated by a reference detector not influenced by the sample to be analyzed, and therefore by allowing compensation for any drift in the light source, for example a temperature-dependent drift, this system is compatible with an application in the field of measurements in difficult environments.

However, the cost of such a spectrometer is determined by the number of light emitting diodes installed, which is directly related to the number of wavelengths to be measured. If this number is substantially larger than six, it becomes too expensive for an on-vehicle unit.

In addition, a source created by juxtaposition of many light emitting diodes may no longer be considered as being a point source, thereby causing detector measurement errors (problems with parallax).

Moreover, the Sentelligence device has to be modified at the design stage for each particular application, thereby requiring measurements at certain wavelengths specific to the sample to be analyzed.

These spectrometers do not allow a high-precision spectral measurement to be obtained, such as that required by certain applications in the automotive field, i.e. for example measurement of the absorption at a given wavelength ±5 nm with a precision of 1% of the given absorption value. They also do not allow use over a wide temperature range.

These various restrictions make these spectrometers unsuitable to use in the context of automobile-borne applications such as the measurement of the chemical composition of a fuel or its precise combustion properties.

SUMMARY OF THE INVENTION

The aim of the present invention is therefore to provide a mini-spectrometer design meeting size, reliability and performance constraints compatible with automobile applications.

A second aim of the invention is to make low-cost production possible making its use in an automotive vehicle feasible.

A third aim is to provide a vehicle-borne spectrometer that may be used for a number of applications to different fluids, without hardware modification.

For this purpose, one first subject of the invention is a device for measuring a spectrum of a light beam, in a wavelength range chosen beforehand, said spectrum being generated by a sample to be analyzed, said optical measuring device comprising:
- at least one light source;
- a measurement cell;
- a measurement detector placed on a measurement optical pathway, said measurement optical pathway being taken by a measurement optical beam emitted by the light source, and encountering the measurement cell,
- self-calibration means allowing any drift of the light source, due to environmental conditions or conditions of use, to be compensated independently of whether a sample to be analyzed is present in or absent from the measurement cell, said self-calibration means comprising:
  - means for creating a reference optical pathway, taken by a reference optical beam emitted by the light source, and not encountering the measurement cell; and
  - a reference detector.

Said measurement device is remarkable in that it is designed to be borne by an automotive vehicle and in that it comprises means for selectively mixing the measurement optical beam and the reference optical beam, and in that the measurement detector also acts as the reference detector.

Preferably, the device measures an absorption spectrum for the light beam absorbed by the sample to be analyzed.

In another embodiment, the device measures a reflection spectrum for the light beam reflected by the sample to be analyzed.

According to a preferred embodiment, the device also comprises at least one wavelength filter associated with the reference detector, said wavelength filter being a variable, Fabry-Perot-cavity interference filter.

Advantageously in this case the device also comprises means of converting the light beam emitted by the light source into a parallel beam.

According to a particular embodiment, the measurement cell comprises means for returning the measurement optical beam in a direction substantially opposed to its original direction.

According to an advantageous embodiment, the means for returning the measurement optical beam comprise two facets oriented at 90° to each other, placed on a lateral side of said measurement cell.

In the case of an absorption spectrometer, the facets advantageously form an overall concave surface within the fluid flow stream in the measurement cell and are made reflective by metalization.

In the case of a reflection spectrometer, the facets advantageously form an overall convex surface within the fluid flow stream in the measurement cell, and are transparent in the wavelength range studied.

It is understood that this arrangement corresponds to the particular case of a reflection spectrometer in which the light rays are simply reflected by the sample analyzed, in contrast to the preceding case corresponding to an absorption spectrometer in which the light rays pass through the sample to be analyzed.

In an advantageous embodiment, the means for creating a reference optical pathway comprise a first beam splitter, and the means for selectively mixing the measurement optical beam and the reference optical beam comprise a second beam splitter and a beam shutter that is activated on command, said beam shutter being placed on the reference optical beam between the two beam splitters.

More particularly, in this case, the two beam splitters are optical cubes comprising, on their diagonal plane, a semi-reflecting mirror.

In another method of implementation, the means for creating a reference optical pathway comprise a first beam splitter that is activated on command, in that the means for selectively mixing the measurement optical beam and the reference optical beam comprise a second beam splitter and a means for controlling the activation of the first beam splitter.

According to an advantageous embodiment, the spectrometer is made of two separable units, a first unit comprising the light source, the beam splitters, the beam shutter and the detectors and thus forming the measurement instrument, and a second unit comprising the measurement cell provided with its facets for returning the measurement optical beam in a direction substantially opposed to its original direction.

A second subject of the invention is a sensor of fuel, oil, coolant or urea quality intended to be permanently installed in a vehicle.

A third subject of the invention is a method for controlling at least one operating parameter of a vehicle engine, said vehicle being provided with a sensor as described above and with an electronic control unit connected to said sensor,
characterized in that it comprises steps of:
- selecting the fluid to be analyzed;
- turning the light source on at regular intervals;
- waiting for a suitable period of time taking account of the normal initialization time of said light source;
- controlling the variable filter so as to set said filter in succession to various wavelengths forming a series necessary for determining the composition of the fluid analyzed, these wavelengths being stored beforehand in a memory of said control unit for each fluid likely to be analyzed by the sensor;
- blocking the reference beam;
- measuring, for each wavelength selected, using the measurement detector, the light intensity received at this wavelength;
- and, at predetermined intervals,
  - allowing the reference beam to pass and be mixed in the second splitter;
  - measuring, for each wavelength selected, using the measurement detector, the combined light intensity received at this wavelength;
- transmitting to the control unit measurements of the absorption spectrum of the fluid to be analyzed and measurements of the combined spectrum;
- comparing, using the control unit, the measurement value and the combined value;
- determining, using the control unit, the absorption due to the sample contained in the measurement cell;
- determining, based on an algorithm or a table of values stored in memory, using the control unit, at regular intervals, modifications to the operating parameters of the engine.

It is understood that the control unit functions are carried out either by an engine control unit or by electronics associated with the sensor, the data transmitted to the engine control unit then corresponding directly to the value of the parameters of the fluid.

Another subject of the invention is a piece of software able to implement the method described.

Finally, the last subject of the invention is a vehicle implementing a device such as described, or a method such as described.

BRIEF DESCRIPTION OF THE DRAWING FIGURES

Objects and advantages of the invention will be better understood on reading the description and drawings of a particular embodiment, given by way of nonlimiting example and for which the drawings show the following.

DETAILED DESCRIPTION OF THE INVENTION

Figure 10:
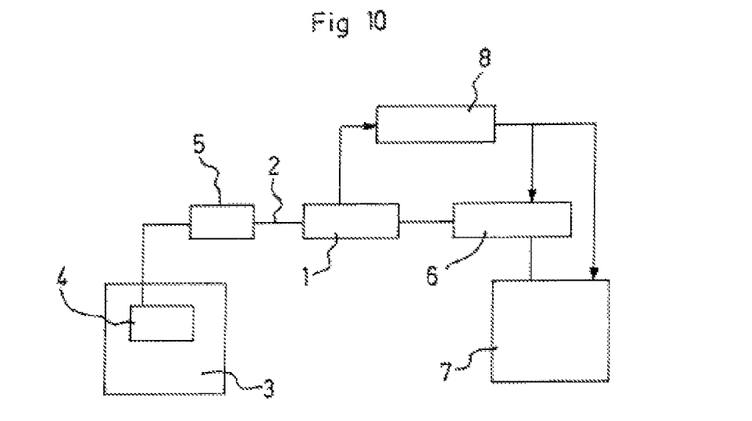
FIG. 10 illustrates the integration of a spectrometer according to the invention into a fuel circuit of an automotive vehicle.

As may be seen in FIG. 10, in the case of an application of a device for measuring absorption spectra according to the invention to a fuel circuit of an automotive vehicle, such a spectrometer 1 may advantageously be placed on a fuel pipe 2, downstream of the tank 3 of the fuel pump 4, also downstream of the fuel filter 5 (so as to reduce measurement errors), but upstream of the injection pump 6 and of the engine 7.

The spectrometer 1 is connected to an electronic control unit 8, which is also connected to the injection pump or to the engine certain settings of which it is able to control. It is noted that this electronic control unit 8 can be either the engine control unit, conventionally present in automotive vehicles, or a control unit of the spectrometer, which sends the values of the parameters of the fluid analyzed directly to the engine control unit.

Figure 5:
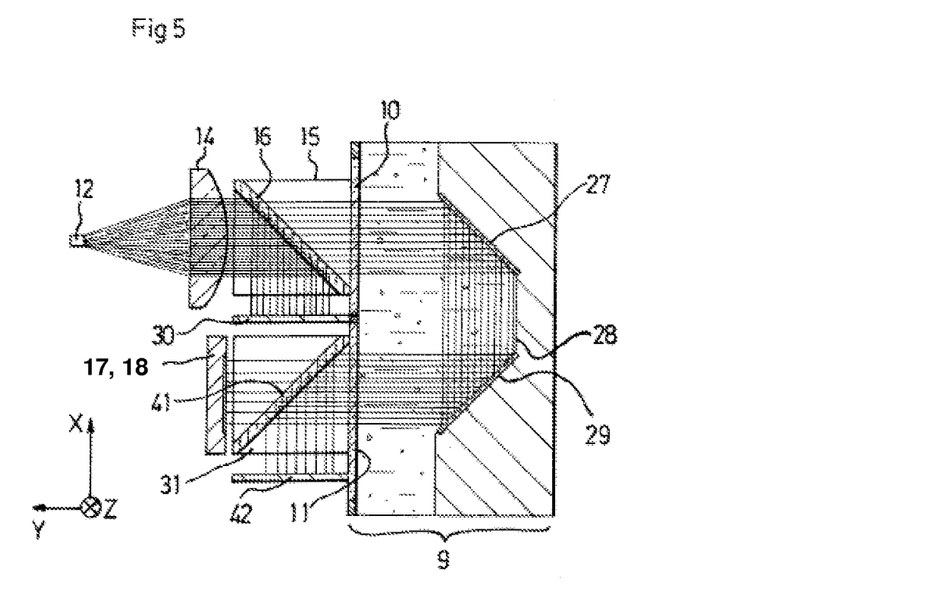
FIG. 5 is a functional schematic representation of a mini-spectrometer according to the invention for a difficult environment, viewed from above.
Figure 6:
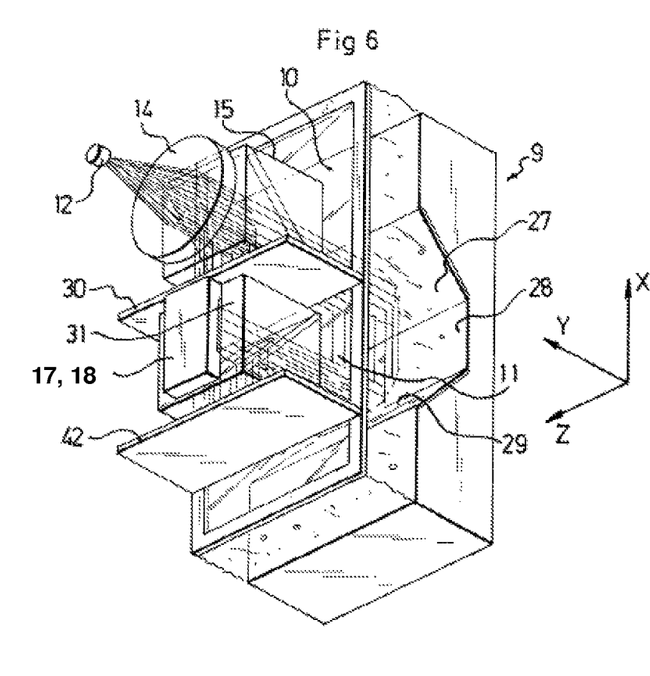
FIG. 6 is an isometric perspective view of the same spectrometer.
Figure 7:
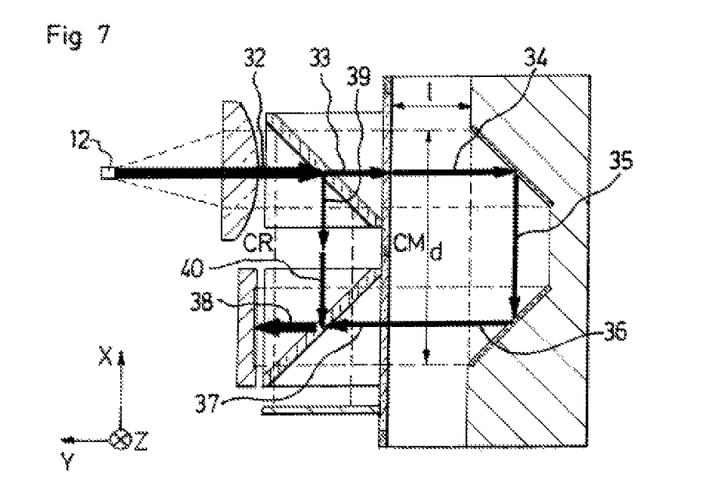
FIG. 7 schematically illustrates the operation of the spectrometer in the case where the shutter is open.

The device according to the invention is illustrated in FIGS. 5 to 7.

The spectrometer 1 according to the invention is organized about a measurement cell 9 in which the fluid, for example fuel, to be analyzed flows.

A longitudinal axis X corresponding to the flow direction of the fluid in the measurement cell 9 is defined for the rest of the description.

This measurement cell 9 is here shown in the form of a segment of tube of rectangular cross section (FIG. 6), oriented substantially along the longitudinal axis X.

It comprises on one of its two lateral sides (left-hand side in FIG. 5) two rectangular, coplanar windows 10, 11 of substantially identical size.

The latter may be made for example of glass or plastic, and this material must be chemically neutral with respect to the fluid analyzed, undeformable as a function of temperature, and transparent in the wavelength range used for the measurement (here the near infrared, but wavelength ranges in the UV/visible may also be used without modification to the device described).

The windows 10, 11 are fixed to the wall of the measurement cell 9 by bonding or any other known means.

A transverse axis Y, normal to the two windows 10, 11, is defined for the rest of the description.

On its opposite lateral side (right-hand side in FIG. 5), a region for reflecting the light, comprising two reflective facets 27, 29, oriented at 90° to each other, allows a light beam entering via a first window 10 (therefore in a direction oriented along the −Y axis), to be returned towards the second window 11 (in a direction oriented along the +Y axis). The two reflective facets 27, are in the present example formed of planar surfaces, oriented, in the case of the first, at 45° in the XY plane and, in the case of the second, at 135° in the same plane.

They are separated by a facet 28, mainly planar and parallel to the longitudinal axis X.

The two reflective facets 27, 29 are dimensioned so as to return all of a light beam emerging from the first window 10 towards the second window 11.

Their reflective character is, in the present embodiment, obtained by polishing and local metalization (for example with chromium) of the surface forming the lateral side of the measurement cell 9, this metalization being carried out by means known to a person skilled in the art. These facets may also be obtained by bonding mirrors onto the sides oriented at 45° and 135°, or by any other suitable means.

The measurement cell 9 is made of metal or a rigid plastic, so that the two windows 10, 11 remain coplanar independently of environmental conditions (in particular temperature), and so that likewise the two reflective facets 27, 29 remain oriented at 90° to each other, the aim being to maintain the path of a light beam passing through the measurement cell 9, and therefore to avoid the creation of measurement errors.

The measurement cell 9 is connected at its two open ends, by means known to a person skilled in the art, to a tube for circulating fuel, previously installed in the vehicle.

In order to measure the absorption spectrum, a light beam passes through the two windows 10, 11 and the fluid contained in the measurement cell 9 and is reflected by the reflective facets of the measurement cell.

This light beam is created by a light source 12, the emission spectrum of which naturally corresponds to the wavelength range appropriate to the fluid to be analyzed.

In the present, nonlimiting case, the light source 12 is formed by three light emitting diodes (LEDs) arranged, in a triangle, as close to one another as possible, on the same holder, perpendicular to the transverse axis Y (oriented towards the measurement cell 9), so as to minimize measurement shifts related to the distance between the three light emitting diodes.

Figure 8:
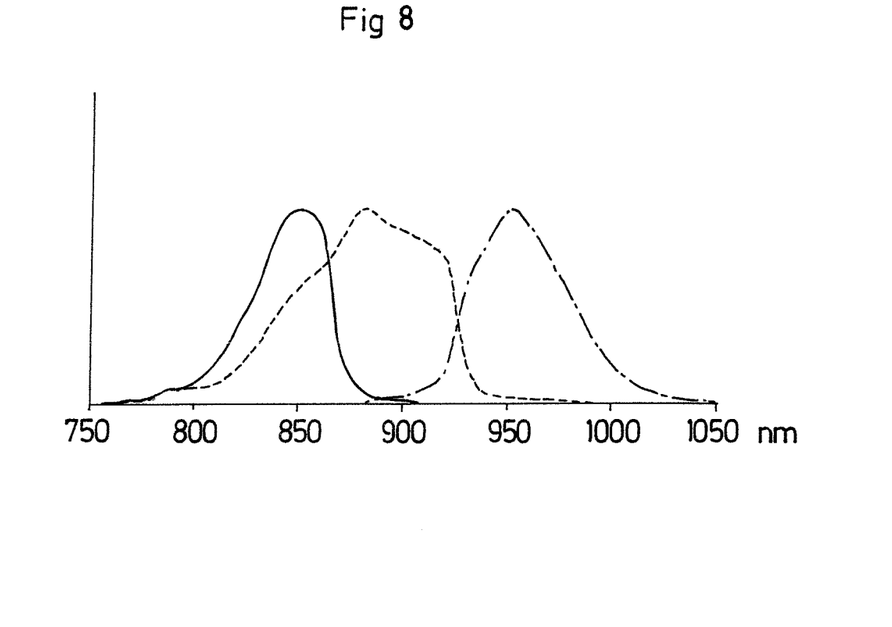
FIG. 8 illustrates the emission spectra of three different light emitting diodes in the near infrared (700-1050 nm)

Their emission peaks are respectively located about 850 nm, 900 nm and 950 nm. As may be seen in FIG. 8, which illustrates the respective emission spectra at 25° C., each of these light emitting diodes has an emission spectrum extending at half-maximum over about 100 nm.

Figure 9:
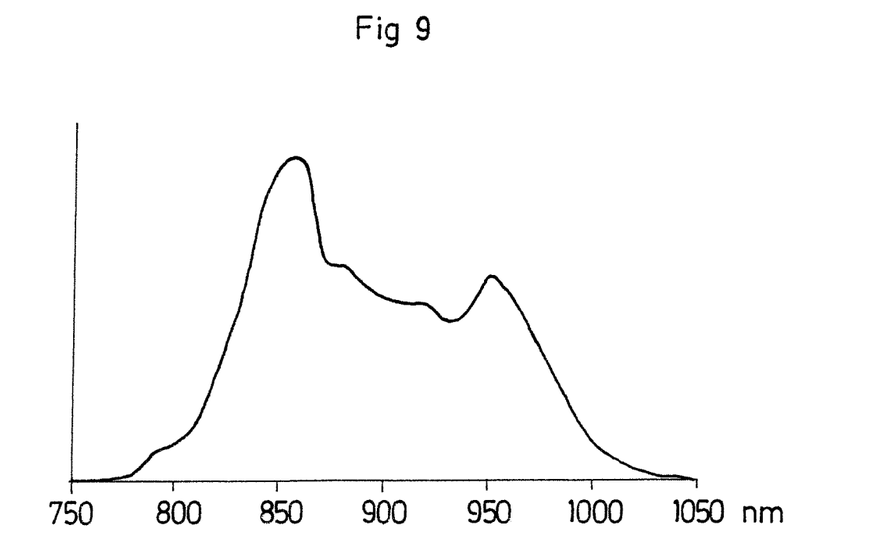
FIG. 9 illustrates the addition of the three normalized spectra of FIG. 8.

The superposition of the three spectra, illustrated in FIG. 9, shows the spectrum equivalent to the complete source. This light source 12 effectively covers a wavelength range from 825 to 975 nm (near infrared).

Clearly other diodes can be used, either, depending on technical advances made in the art, by using diodes that have a low unit cost but offer a wider spectrum or with the aim of creating a spectrum in another wavelength range.

It is understood that the light emitting diodes chosen are commercially available products having a very low unit cost. An equivalent light source 12 has therefore been created based on available components that are very cheap, with the aim of minimizing the overall cost of the spectrometer 1. Moreover, light emitting diodes are known to have a lifetime (period of time before the power emitted has halved) of several tens of thousands of hours, therefore compatible with the lifetime required of an automotive-vehicle-borne instrument.

These three light emitting diodes, the combined power of which does not exceed a few tenths of a watt, are supplied with power by known means, details of which are not given here.

The light beam created by the light source 12 has an overall conical shape having an angle set by the light emitting diodes chosen, in the present example being about a few tens of degrees.

This beam is optionally restricted to a circular beam (or a beam having a shape chosen beforehand) of smaller width in space by an aperture, for example a known mechanical device.

After passing through the aperture, the light beam, still conical at this point, is transformed into a parallel beam of cylindrical cross section by a collimating lens 14. This collimating lens 14 is of known (for example planar/convex) type and may be made of glass or plastic of high optical quality at the wavelengths measured. Its dimensions allow a beam of one tenth to a few tenths of cm$^2$ to be created.

This collimation of the light, which renders the rays thereof parallel, is particularly important for the quality of the measurement, particularly in the case where an "interference filter" technology is used, as will be seen below.

The spectrometer according to the invention comprises, downstream of the collimating lens 14, a beam splitter 15, intended to separate the light beam (illustrated by the segment 32 in FIG. 7) into, on the one hand, a measurement beam following a measurement optical pathway CM, parallel to the transverse axis Y (segment 33 in FIG. 7), and, on the other hand, a reference beam following a reference optical pathway CR, overall parallel to the longitudinal axis X (segment 39, in FIG. 7).

This beam splitter 15 is an optical component allowing for example 50% of the light to pass and reflecting 50% in a direction at 90° to the original beam. It is for example an optical cube comprising, on its diagonal plane, oriented at 45° in the XY plane, a semi-reflecting mirror 16. Therefore, the two beams created here are considered to have the same spectrum (wavelengths and power emitted at each wavelength). The light transmitted through the mirror is directed towards the measurement cell 9. Its method of manufacture is known to a person skilled in the art and therefore details are not given here. It may also be a birefringent mirror.

The beam splitter 15 is placed in the immediate vicinity, even directly in contact with the first window 10 of the measurement cell 9 so as to minimize the path of the optical beam outside of the fluid to be studied.

The measurement beam, as is clearly illustrated in FIG. 7, therefore passes through this first window 10, and through a thickness of fluid to be analyzed, which thickness depends on the width 1 of the measurement cell along the transverse axis Y and on the distance d between the ends of the reflective facets according to the formula 2l+d.

After this optical path (illustrated by the segments 34, 35 and 36 in FIG. 7 for a light ray located at the centre of the beam) within the fluid analyzed in the measurement cell 9, the light beam exits from said measurement cell 9 by passing through the second window 11. While traveling within the fluid analyzed, certain wavelengths of the emission spectrum of the light source 12 are attenuated due to absorption of photons at these wavelengths by molecules present in the fluid.

The measurement beam, the spectrum of which has been modified by the passage through the fluid, exits the measurement cell 9 along the transverse axis Y and passes through a second beam splitter 31, placed in the immediate vicinity, even directly in contact with the second window of the measurement cell 9, here again to minimize the path of the optical beam outside of the fluid to be studied.

This second beam splitter 31 is intended here to mix the measurement beam which followed the measurement optical pathway CM (segments 33 to 37 in FIG. 7), and the reference beam which followed a reference optical pathway CR (segments 39 and 40 in the FIG. 7), into a single light beam (segment 38 in FIG. 7).

This second beam splitter 31 is an optical component similar to the first beam splitter 15, allowing for example 50% of the light to pass and reflecting 50% in a direction at 90° to the original beam. It is for example an optical cube comprising on its diagonal plane, oriented at 135° in the XY plane, a semi-reflecting mirror 41.

It is understood that the second beam splitter 31 is placed at the intersection of the measurement optical pathway CM and the reference optical pathway CR. It is in the present example aligned with the first splitter 15 along the longitudinal axis X. The distance between the centers of the semi-reflecting mirrors 16, 41 is substantially equal to the distance between the centers of the reflective facets 27, 29 of the measurement cell 9.

The device according to the invention also comprises, placed on the reference optical pathway CR between the two beam splitters 15, 31, a beam shutter 30 of a sort known per se and that can be activated on command by an electrical means. This beam shutter 30 allows the reference beam to pass or prevents it from passing (segment 39 in FIG. 7) to the second beam splitter 31 (segment 40 in FIG. 7 when the shutter 30 is open), on command.

This shutter is an electromechanical or electro-optical (for example liquid crystal) shutter, chosen for example depending on the environmental conditions in which the spectrometer must be used.

The light beam 38, output by the second beam splitter 31, and comprising either the measurement light beam alone or the measurement beam and the reference beam combined, is finally sensed by a measurement detector 17 equipped with a wavelength filter.

These filters are, in the preferred embodiment described here, Fabry-Perot interference cavities—and in this case the wavelength capable of passing through depends, as is known, on the width of this cavity and therefore on the angle of incidence of the light rays. It is understood that it is therefore desirable, for a precise measurement, for the light rays to be truly parallel. This justifies the use of the collimating lens 13.

Figure 11:
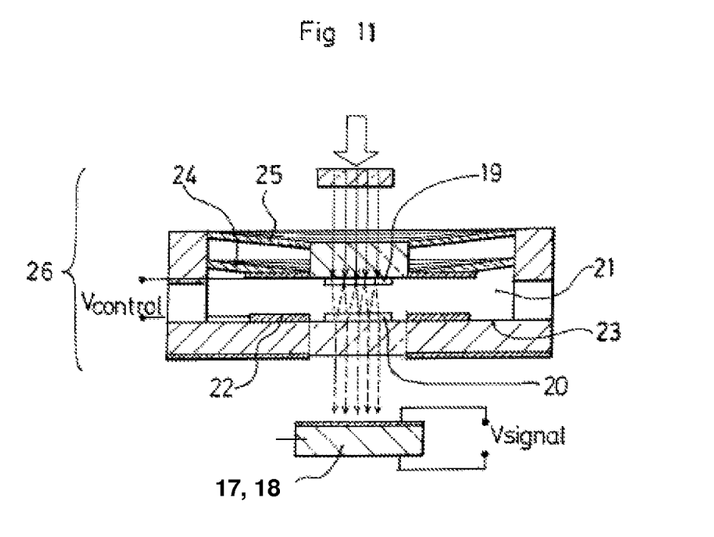
FIG. 11 schematically illustrates the design principle of a detector combined with a filter that can be activated on command.

The measurement detector 17, which can also serve as a reference detector 18, is equipped with a variable filter 26, for example a Fabry-Perot cavity filter, of the sort presented in the document "Tunable infrared detector with integrated micromachined Fabry-Perot filter" (Neumann, Ebermann, Hiller, Kurth, MOEMS January 2007), and illustrated in FIG. 11.

The measurement detector 17 is placed on the measurement optical pathway CM at the output of the variable filter 26. It is a pyroelectric detector in the present example, thereby having a very short response time, but it may be replaced with a linear variable filter (LVF) or one or more optical filters associated with a charge coupled device (CCD) or complementary metal oxide semiconductor (CMOS) matrix.

In operation, when the control unit 8 associated with the spectrometer 1 has been initialized for a fluid to be analyzed (selection of the wavelengths to be observed), the control unit 8 turns on the light source 12 at regular intervals the spacing of which has been chosen beforehand.

After a suitable period of time taking account of the normal initialization time of said light source, the control unit controls the potential difference between the plates of the Fabry-Perot interference filters (or controls the means of making the value of the variable filter vary) so as to set said filters in succession to various wavelengths forming a series necessary for determining the composition of the fluid analyzed, these wavelengths being stored beforehand in a memory of said control unit 8.

The control unit 8 then closes the shutter 30 and therefore blocks the reference beam following the optical pathway CR. Only the light beam passing through the measurement cell 9 is therefore sensed by the measurement detector 17.

For each wavelength λ selected, the measurement detector 17 delivers as output a measurement characterizing the light intensity received at this wavelength. The spectrometer 1 thus transmits at regular intervals measurements of the absorption spectrum of the fluid to be analyzed to the control unit 8.

The measurement is then defined by the equation:

$$I_{receiver\_ob}(\lambda) = A \times I_{LED}(\lambda) \times \alpha_{Fuel}(\lambda) \quad \text{(Eq. 1),}$$

in which:
A is the attenuation that occurs along the measurement optical pathway CM running from segment 32 to 38 (losses due to the collimating lens 14, to the beam splitter 15, to the measurement cell 9, and to the second beam splitter 31).

λ is the wavelength studied, $\alpha_{Fuel}(\lambda)$ is the absorption of a known thickness (2l+d) of the fluid analyzed at this wavelength, $I_{LED}(\lambda)$ is the intensity of the light source at this wavelength, and $I_{receiver\_ob}(\lambda)$ is the intensity measured by the detector at this wavelength.

Next at predetermined intervals,
the control unit causes the shutter 30 to open, and therefore causes the reference beam to pass following the reference optical pathway CR, and be mixed in the second splitter 31 with the measurement beam following the measurement optical pathway CM;
at this point, the measurement detector 17 senses, at each wavelength λ selected, the combined light intensity received at this wavelength, and transmits this intensity measurement to the control unit 8.

This measurement is then defined by the equation:

$$I_{receiver\_Nob}(\lambda) = A \times I_{LED}(\lambda) \times \alpha_{Fuel}(\lambda) + B \times I_{LED}(\lambda) \quad \text{(Eq. 2),}$$

in which:
A is the attenuation that occurs along the measurement optical pathway CM and B is the attenuation that occurs along the reference optical pathway CR (pathway that does not pass through the fluid analyzed) running through segments 32, 39, 40, 38 (losses due to the collimating lens 14, to the beam splitter 15 and to the second beam splitter 31).

It is noted that the influence of temperature and aging on these attenuation values A and B is a priori negligible, which values are known as of the manufacture of the spectrometer and remain fixed over time.

The control unit 8 compares the measurement value and the combined value and derives therefrom, first by subtracting the two equations, the term $B \times I_{LED}(\lambda)$ and therefore, B being known, the light intensity delivered by the light emitting diode at this wavelength under these environmental and aging conditions of the LED, and then, by reintroducing this intensity into the equation Eq. 1, the absorption $\alpha_{Fuel}(\lambda)$ due to the sample contained in the measurement cell 9 at this wavelength under these environmental conditions.

Based on an algorithm or a table of values stored in memory the control unit 8 determines, at regular intervals, modifications to operating parameters of the engine 7, for example whether the fuel conforms to a type suitable for the operation of the engine, setting of the ignition advance, setting of the injection, etc.

The processing of the signal output from the spectrometer according to the invention is beyond the scope of the present invention, and it is therefore not described in greater detail.

The first advantage of the spectrometer according to the invention is the use of a single detector, used both for the reference beam and for the measurement beam, thanks to the use of a reflector in the cell, and of a beam shutter on the reference optical pathway.

This allows the cost of the sensor to be reduced, the detector and the associated variable filter making up a very significant part of the overall cost of said sensor. Moreover, this design performs better since the two signals (measurement and reference+measurement) which are compared are measured by the same detector, thereby eliminating systematic errors that could possibly be due to the detector. Finally, the control electronics of the sensor are also simplified, since they control only one detector instead of two, thereby further contributing to the reliability of the system and reducing the cost thereof.

A second advantage of the device is that the optical and optoelectronic components are grouped on the same side of the measurement cell. Thus, the spectrometer may be organized in two separate functional units. Moreover, this makes it possible to produce a smaller circuit board, one of the sides of the measurement cell not requiring connection.

A third advantage of the present invention is the use of a reference optical pathway. This allows the effects of aging and variations in environmental conditions on the diodes forming the light source to be compensated for. In addition, the measurement cell does not need to be emptied to obtain a reference measurement, which may be carried out at any moment.

Among the applications which may be considered for the spectrometer described above, mention may naturally be made of a vehicle-borne sensor of vehicle-borne fuel, oil, coolant or urea quality.

More generally, such a proposed device is applicable to any measurement of fluid quality carried out in difficult environments (temperature, physical access, etc.).

The scope of the present invention is not limited to the detailed embodiments considered above by way of example, but in contrast extends to modifications within the competence of a person skilled in the art.

The description given concerns a transmission spectrometer, for which the spectrum measured is the spectrum of the light having passed through the sample. The principle described is equally applicable to a reflection spectrometer, measuring the light reflected by a sample.

In this case, the reflective facets 27, 29, oriented at 90° to each other, form an overall convex surface within a fluid flow stream, instead of an overall concave shape such as described above. Naturally they are no longer metalized, but on the contrary are transparent in the wavelength range studied, the aim being to measure the reflection spectrum of the fluid flowing through the measurement cell 9.

It is understood that the spectrometer such as described is composed of two main units, with on the one hand the light source, the beam splitters and the detectors forming the measurement instrument, and on the other hand the measurement cell provided with its reflective facets. These two units may be made of elements manufactured separately and subsequently assembled.

In this way, the choice of a transmission (case described above) or reflection spectrometer operating mode may be made at the last minute. It may even be envisioned to supply the measurement unit with two units forming different measurement cells suitable for the two operating modes, the user choosing to install the unit forming the measurement cell meeting his requirements.

As a variant, the two reflective facets 27, 29 may be replaced by any device returning the light at 180° to its original direction, and for example by a parabolic reflector, or by a surface formed of more than two reflective facets.

Similarly, the two reflective facets 27, 29 may have a common edge, eliminating the intermediate surface 28.

In another variant, the forming optic (collimating lens) 14 is placed near the detector, instead of being placed immediately after the light source 12 (and optionally the aperture 13). This arrangement preserves the parallel alignment of the light rays in the detector 17.

In yet another variant, the first beam splitter 15 can be activated on command (for example it is a liquid-crystal or electrical birefringent mirror 16) and therefore replaces the shutter 30. When it is not activated the light beam follows the measurement optical pathway CM and passes through the measurement cell 9. In contrast, when this mirror 16 that can be activated on command is activated, the light beam is divided by the first splitter 15 into a measurement optical beam and a reference optical beam, and these beams are recombined by the second splitter 31. The operation of the spectrometer is unchanged overall.

In another variant, the measurement cell 9 does not comprise a reflector with facets 27, 29 and the light passes through the measurement cell 9 from end to end. A light reflection device, external to the measurement cell 9, allows the measurement beam to be returned towards the detector 17. The operation of the device here remains substantially unchanged.

In a variant light source 12, the latter is formed by four light emitting diodes (LEDs) arranged in a square, as close to one another as possible.

The invention claimed is:

1. An optical measuring device (1) for an automotive vehicle, adapted for measuring a spectrum of a light beam, in a wavelength range chosen beforehand, said spectrum being generated by a sample to be analyzed, said optical measuring device comprising:
   at least one light source (12);
   an optic (14) for forming light rays emitted by said at least one light source (12);
   a measurement cell (9); and
   a measurement detector (17) placed on a measurement optical pathway, said measurement optical pathway being taken by a measurement optical beam emitted by the at least one light source (12), and encountering the measurement cell (9),
   a self calibrator allowing any drift of the light source (12), due to environmental conditions or conditions of use, to be compensated independently of whether a sample to be analyzed is present in or absent from the measurement cell (9), said self calibrator comprising:
      means (15) for creating a reference optical pathway, taken by a reference optical beam emitted by the light source (12), and not encountering the measurement cell (9); and
   a reference detector (18) that is also the measurement detector (17),
   means (30, 31) for selectively mixing the measurement optical beam and the reference optical beam,
   wherein the means for creating a reference optical pathway comprise a first beam splitter (15), and in that the means for selectively mixing the measurement optical beam and the reference optical beam comprise a second beam splitter (31) and a beam shutter (30) that is activated on command, said beam shutter (30) being placed on the reference optical beam between the two beam splitters (15, 31).

2. The device as claimed in claim 1, further comprising at least one wavelength filter associated with the reference detector (17).

3. The device as claimed in claim 2, wherein the wavelength filter is a variable filter (26) and means for varying the value of the variable filter (26).

4. The device as claimed in claim 1, wherein the measurement cell (9) comprises means (27, 29) for returning the measurement optical beam in a direction substantially opposed to an original direction.

5. The device as claimed in claim 4, wherein the means for returning the measurement optical beam comprise two facets (27, 29) oriented at 90° to each other, placed on a lateral side of said measurement cell (9).

6. The device as claimed in claim 1, wherein the means for creating a reference optical pathway comprise a first beam splitter (15) that is activated on command, and the means for selectively mixing the measurement optical beam and the reference optical beam comprise a second beam splitter (31) and a means for controlling the activation of the first beam splitter (15).

7. The device as claimed in claim 4, wherein the device is made of two separable units, including a first unit comprising the light source (12), the beam splitters (15, 31), the beam shutter (30) and the detectors (17) and thus forming the measurement instrument, and a second unit comprising the measurement cell (9) provided with facets (27, 29) for returning the measurement optical beam in a direction substantially opposed to its original direction.

8. A sensor of fuel, oil, coolant or urea quality intended to be permanently installed in a vehicle, comprising a measurement device (1) as claimed in claim 1.

9. A vehicle, comprising a sensor as claimed in claim 8.

10. The device according to claim 1, wherein for each wavelength λ selected, the measurement detector (17) is configured to deliver as output a measurement characterizing the light intensity received at this wavelength, and the device thus transmits at regular intervals measurements of the absorption spectrum of the fluid to be analyzed to the control unit (8), and the measurement is defined by equation 1:

$$I_{receiver\_ob}(\lambda) = A \times I_{LED}(\lambda) \times \alpha_{Fuel}(\lambda) \quad (Eq. 1),$$

in which:
A is the attenuation that occurs along the measurement optical pathway,
λ is the wavelength studied,
$\alpha_{Fuel}(\lambda)$ is the absorption of a known thickness (2l+d) of the fluid analyzed at this wavelength,
$I_{LED}(\lambda)$ is the intensity of the light source at this wavelength, and
$I_{receiver\_ob}(\lambda)$ is the intensity measured by the detector at this wavelength.

11. The device according to claim 1, wherein at predetermined intervals
the control unit causes the shutter (30) to open, and therefore causes the reference beam to pass following the reference optical pathway, and be mixed in the second beam splitter (31) with the measurement beam following the measurement optical pathway; and
at this point, the measurement detector (17) senses, at each wavelength λ selected, the combined light intensity received at this wavelength, and transmits the combined light intensity measurement to the control unit (8), and is defined by equation 2:

$$I_{receiver\_Nob}(\lambda) = A \times I_{LED}(\lambda) \times \alpha_{Fuel}(\lambda) + B \times I_{LED}(\lambda) \quad (Eq. 2),$$

in which:
A is the attenuation that occurs along the measurement optical pathway, and
B is the attenuation that occurs along the reference optical pathway.

12. A method for controlling at least one operating parameter of a vehicle engine, said vehicle being provided with a sensor as claimed in claim 8 and with an electronic control unit (8) connected to said sensor,
comprising:
selecting the fluid to be analyzed;
turning the light source (12) on at regular intervals;
waiting for a period of time taking account of the normal initialization time of said light source (12);
controlling the variable filter (26) so as to set said filter in succession to various wavelengths forming a series necessary for determining the composition of the fluid analyzed, these wavelengths being stored beforehand in a memory of said control unit (8) for each fluid likely to be analyzed by the sensor;
blocking the reference beam;
measuring, for each wavelength selected, using the measurement detector (17), the light intensity received at this wavelength;
and, at predetermined intervals,
allowing the reference beam to pass and be mixed in the second splitter (31);
measuring, for each wavelength selected, using the measurement detector (17), the combined light intensity received at this wavelength;
transmitting to the control unit (8) measurements of the absorption spectrum of the fluid to be analyzed and measurements of the combined spectrum;
comparing, using the control unit (8), the measurement value and the combined value;
determining, using the control unit, the absorption due to the sample contained in the measurement cell (9);
determining, based on an algorithm or a table of values stored in memory, using the control unit (8), at regular intervals, modifications to the operating parameters of the engine (7).

13. A software product, comprising program code instructions recorded on a non-transient computer readable medium, for implementing the steps of the method as claimed in claim 12 when said software product is run on a computer.

14. A spectrometer for a vehicle, adapted for measuring a spectrum of a light beam, in a wavelength range chosen beforehand, said spectrum being generated by a sample to be analyzed, said spectrometer comprising:
at least one light source;
an optic for forming light rays emitted by said at least one light source;
a measurement cell; and
a measurement detector placed on a measurement optical pathway, said measurement optical pathway being taken by a measurement optical beam emitted by the at least one light source, and encountering the measurement cell,
a self calibrator allowing any drift of the light source, due to environmental conditions or conditions of use, to be compensated independently of whether a sample to be analyzed is present in or absent from the measurement cell, said self calibrator comprising:
a first beam splitter configured for creating a reference optical pathway, taken by a reference optical beam emitted by the at least one light source, and not encountering the measurement cell; and
a reference detector that is also the measurement detector,
a second beam splitter configured for selectively mixing the measurement optical beam and the reference optical beam; and
a beam shutter that is adapted to be activated on command, said beam shutter being placed on the reference optical beam between the first and beam splitters.

15. The spectrometer as claimed in claim 14, further comprising at least one wavelength filter associated with the reference detector.

16. The spectrometer as claimed in claim 15, wherein the wavelength filter is a variable filter.

17. The spectrometer as claimed in claim 14, wherein the measurement cell comprises reflective facets configured for returning the measurement optical beam in a direction substantially opposed to an original direction.

18. The spectrometer as claimed in claim 17, wherein the facets comprise two facets oriented at 90° to each other, placed on a lateral side of said measurement cell.

19. The spectrometer as claimed in claim 17, wherein the device is made of two separable units, including a first unit comprising the light source, the first and second beam splitters, the beam shutter and the detector, and a second unit comprising the measurement cell provided with the facets.

20. The spectrometer according to claim 14, wherein for each wavelength λ selected, the measurement detector is configured to deliver as output a measurement characterizing the light intensity received at this wavelength, and the device thus transmits at regular intervals measurements of the absorption spectrum of the fluid to be analyzed to the control unit, and the measurement is defined by equation 1:

$$I_{receiver\_ob}(\lambda) = A \times I_{LED}(\lambda) \times \alpha_{Fuel}(\lambda) \quad (Eq. 1),$$

in which:

A is the attenuation that occurs along the measurement optical pathway, $\lambda$ is the wavelength studied, $\alpha_{Fuel}(\lambda)$ is the absorption of a known thickness (2l+d) of the fluid analyzed at this wavelength, $I_{LED}(\lambda)$ is the intensity of the light source at this wavelength, and $I_{receiver\_ob}(\lambda)$ is the intensity measured by the detector at this wavelength.

* * * * *